United States Patent [19]

Wittman et al.

[11] Patent Number: 5,412,082
[45] Date of Patent: May 2, 1995

[54] CONVERSION OF AMINES TO HYDROXYLAMINES

[75] Inventors: Mark D. Wittman, Hamden; Samuel J. Danishefsky; Randall L. Halcomb, both of New Haven, all of Conn.

[73] Assignee: Yale University, New Haven, Conn.

[21] Appl. No.: 114,601

[22] Filed: Aug. 31, 1993

Related U.S. Application Data

[63] Continuation of Ser. No. 498,106, Mar. 23, 1990, abandoned.

[51] Int. Cl.[6] .................... C07H 19/02; C07C 239/00
[52] U.S. Cl. .................... 536/17.2; 536/17.9; 536/18.7; 536/55.1; 530/300; 564/32; 564/300; 564/301
[58] Field of Search .......... 536/17.2, 17.9, 22; 530/300; 564/32, 300, 301

[56] References Cited

U.S. PATENT DOCUMENTS 5,001,233  3/1991  Murray et al. .................... 564/301

OTHER PUBLICATIONS

Murray et al., *Synthetic Communications*, 19(20):3509–3522 (1989).
Wittman et al., *J. Org. Chem.*, 55:1980 (Mar. 1990).
*The Merck Index*, tenth ed., p. 2810, 4746.
Murray et al., *Tetrahedron Lett.*, 29:4677 (1988).
Murray et al., *Tetrahedron Lett.*, 27:2335 (1986).
Zabrowski et al., *Tetrahedron Lett.*, 29:4501 (1988).
Murray et al., *J. Org. Chem.*, 50:2847 (1985).
Murray et al., *J. Org. Chem.*, 54:5783 (1989).
Adam et al., *J. Org. Chem.*, 52:2800–2803 (1987).
March, *Advanced Organic Chemistry*, Third ed., p. 1086.
Wittman et al., *J. Org. Chem.*, 55:1981–1983 (1990).

*Primary Examiner*—David A. Redding
*Assistant Examiner*—Everett White
*Attorney, Agent, or Firm*—Dressler, Goldsmith, Shore & Milnamow, Ltd.; Martin L. Katz

[57] ABSTRACT

Oxidation of primary amines to primary hydroxylamines using a dialkyl dioxirane is described. This new method is utilized to prepare aliphatic non-axial hydroxylamines from corresponding primary amino-substituted sugar derivatives and hydroxylamino acid derivatives.

13 Claims, 6 Drawing Sheets

CONVERSION OF AMINES TO HYDROXYLAMINES

This invention was made with government support under Grant numbers CA 28824 and CA 08641 awarded by the Department of Health and Human Services and CHE 7916210 awarded by the National Science Foundation. The government has certain rights in the invention.

This application is a continuation of application Ser. No. 07/498,106, filed Mar. 23, 1990, now abandoned.

TECHNICAL FIELD

The present invention relates to a novel oxidation of a non-axial amine to its corresponding hydroxylamine, and more particularly to the conversion of biologically interesting amines such as those of sugar derivatives and amino acids to their respective, corresponding hydroxyl amines.

BACKGROUND

Hydroxylamines are an interesting group of compounds if only because they contain two nucleophilic atoms, nitrogen and oxygen, bonded to each other. Indeed, either of the nucleophilic atoms can take part in nucleophilic reactions, depending upon the reactants and substrates. Still further, the nucleophilicity of hydroxylamines is enhanced over that expected on the basis of their $pK_a$ values in what has been termed the "α-effect" [Edwards et al., J. Am. Chem. Soc., 84:16 (1962)].

Aliphatic primary hydroxyl amines; i.e., a hydroxylamine substituted on the nitrogen atom by a single aliphatic organic radical, such as N-methyl hydroxylamine are items of commerce. N-Acylated hydroxyl amines form hydroxamic acids, which can be used in assays for the presence of iron$^{III}$ ions because of the reddish colored complexes that are formed. Primary hydroxylamines also act as ligands to form complexes with metal ions.

Primary hydroxylamines are typically prepared by reaction of hydroxylamine itself with an aldehyde to form an oxime, followed by reduction of the oxime with a mild reducing agent. Primary amines oxidized with Caro's acid ($H_2SO_5$) typically form the corresponding nitrone that rearranges to an oxime, with the hydroxylamine being a postulated intermediate. Secondary amines oxidized with Caro's acid form secondary hydroxylamines.

The usual α-amino acids are also used as ligands to complex with metal ions such as iron. The corresponding α-hydroxylamino acids, and their corresponding hydroximates are also useful as ligands for forming complexes with metal ions such as $Fe^{III}$.

The recently reported calicheamicin [see, Lee et al., J. Am. Chem. Soc., 109:3464 (1987) and the citations therein] and esperamicin [see, (a) Golik et al., J. Am. Chem. Soc., 109:3461 (1987); and (b) Golik et al., J. Am. Chem. Soc., 109:3462 (1987) and the citations therein] antibiotics contain a novel hydroxylamine-substituted glycosidic unit in their oligosaccharide side chains. Inasmuch as the polysaccharide portions of the calicheamicins and esperamicins appear to direct those antibiotics to DNA molecules where they intercalate and cleave the DNA, it would be of interest to synthesize the hydroxylamine-containing sugar derivatives as well as the entire oligosaccharide portion of an esperamicin or a calicheamicin that could be then bonded to the enediyne portion to form a synthetic esperamicin or calicheamicin or derivative thereof.

It would therefore be beneficial if a relatively high yielding, simple synthesis could be devised to form aliphatic primary hydroxylamine compounds. The disclosure below describes one such process for the preparation of aliphatic primary hydroxylamine compounds.

BRIEF SUMMARY OF THE INVENTION

The present invention contemplates the formation of an aliphatic non-axial hydroxylamine from a corresponding non-axial primary amine, and the hydroxylamine products. This method comprises admixing an excess of an aliphatic non-axial primary amine with a dialkyl dioxirane having a total of two to about six carbon atoms in the dialkyl groups to form a reaction mixture. The reaction mixture is maintained for a time period sufficient to form the corresponding hydroxylamine.

Particularly preferred aliphatic non-axial primary amine-containing starting materials are substituted sugar derivatives and amino acid derivatives. A particularly preferred dialkyl dioxirane is dimethyl dioxirane.

The present invention has several benefits and advantages.

One benefit of the invention is that it provides a ready means for the preparation of primary non-axial hydroxylamines.

An advantage of the present invention is that primary non-axial hydroxylamines can be produced in compounds having various substituent groups without substantial alteration of those substituents.

Another benefit of the invention is that an important intermediate in the synthesis of the esperamicin trisaccharide group can be readily prepared.

Still further benefits and advantages will be apparent to a skilled worker from the disclosures that follow.

BRIEF DESCRIPTION OF THE DRAWINGS

In the drawings forming a portion of this disclosure.

DEFINITIONS

The following words and phrases are utilized herein to have the meanings that are normally recognized in the art and as are described below.

The term "sugar" and "sugar derivative" are utilized herein generically to mean a carbohydrate or carbohydrate derivative that contains 5-9 atoms in its backbone chain, and those of interest herein can be a pentose, hexose, heptose, octulose or nonulose.

A "monosaccharide" is a simple sugar that cannot be hydrolyzed into smaller units.

An "oligosaccharide" is a compound sugar that yields two to about 10 molecules of simple monosaccharide per molecule on hydrolysis.

A "polysaccharide" is a compound sugar that yields more than 10 molecules of simple monosaccharide per molecule on hydrolysis.

A sugar molecule or its derivative typically contains a plurality of hydrogen, alkyl, hydroxyl, amine or mercaptan groups in free or protected form such as the N-phthalimido group or the S-acetyl group bonded to each of the carbon atoms of the molecular chain. Where the sugar molecule is in cyclic form, the oxygen atom of one of the hydroxyl groups is utilized as the oxygen that is part of the cyclic ring structure. A deoxysugar contains a hydrogen atom or other substituent group in place of one of the hydroxyl groups.

Each of the substituents, other than the hydrogen of a deoxysugar, has a particular stereochemical configuration relative to the other substituents and relative to the plane of the cyclic ring. The chain length and stereochemical configuration of the substituent groups provide the basis for the names of the sugars. The sugar molecules and their derivatives utilized herein are of known stereochemical configuration.

Position numbering in a sugar molecule begins with the aldehydic carbon for aldoses and the terminal carbon atom closest to the keto group for ketoses. Thus, for a glycal, the first carbon of the ethylenic unsaturation adjacent the ring oxygen is numbered "position 1", with the remaining positions being numbered around the ring away from the ring oxygen atom.

The carbon atom at position 1 is also referred to as the "anomeric atom" or "anomeric carbon atom" due to the possible formation of anomers at that position. Alpha ($\alpha$) anomers are bonded below the plane of the ring in its usually drawn form, whereas in beta ($\beta$) anomers, the bond is above the plane of the ring when so drawn. A substituent at other than the anomeric carbon atom can also be above or below the ring, and thus can also have a $\beta$ or $\alpha$ configuration.

In addition, a substituent can also be said to point sideways or outward from the ring while being held generally in the plane of a six-membered ring, and be in a so-called equatorial configurational position. A substituent can also be generally pointing up or down from the ring and be held at almost right angles to the ring, and said to be in an axial configurational position.

A "glycoside" is a sugar derivative containing a substituent bonded to the anomeric carbon atom. The glycosidic bond can be between the anomeric carbon and an oxygen, nitrogen or sulfur atom and their appropriate other substituents other than hydrogen.

The word "corresponding" is used herein in relation to aliphatic amine derivatives and their reaction products to mean that the substituents present on a reactant compound prior to a given reaction are present in the same configuration after the reaction unless otherwise stated.

DETAILED DESCRIPTION OF THE INVENTION

A. Introduction

One of the many fascinating features of the trisaccharide of esperamicin [(a) Golik et al., *J. Am. Chem. Soc.*, 109:3461 (1987); (b) Golik et al., *J. Am. Chem. Soc.*, 109:3462 (1987)] is the presence of a hydroxylamino sugar glycosidically linked to a sulfur containing sugar. One aspect of this invention is concerned with chemistry designed to produce equatorial hydroxylamino sugars. [For previous syntheses of hydroxylamino sugars see: (a) Tronchet et al., *Helv. Chim Acta*, 69:1132 (1986); (b) Tronchet et al., *Carbohydr. Res.*, 191:138 (1989).]

In particular, hydroxylamino sugars are herein shown to be accessible by direct oxidation of the corresponding equatorial amines. In this way, the relatively well developed capacity for synthesizing amino sugars can be used to good advantage toward our goal systems.

A particularly useful oxidizing agent for this purpose is a dialkyl dioxirane such as 2,2-dimethyl dioxirane—a reagent of increasing importance in synthesis. [(a) Curci et al., *J. Org. Chem.*, 45:4758 (1980); (b) Murray et al., *J. Org. Chem.*, 50:2847 (1985); (c) Adam et al., *J. Org. Chem.*, 52:2800 (1987); (d) Murray, *Chem. Rev.*, 89:1187 (1989); (e) Adam et al., *Acc. Chem. Res.*, 22:205 (1989).] This type of oxidation is shown herein to be useful and practical for forming sugar derivatives having a hydroxylamine substituent, as well as for preparation of hydroxylamine-containing amino acids. [For the oxidation of amines to nitro compounds using 2,2-dimethyldioxirane see: (a) Murray et al., *Tetrahedron Lett.*, 27:2335 (1986); (b) Murray et al., *Tetrahedron Lett.*, 29:4677 (1988); (c) Zabrowski et al., *Tetrahedron Lett.*, 29:4501 (1988); (d) Murray et al., *J. Org. Chem.*, 54:5783 (1989); reference 4(d) cites such an oxidation of a pyrolidine.] No previous reports have been found of an oxidation of a primary amine to a hydroxylamine with a dialkyl dioxirane such as 2,2-dimethyldioxirane.

B. The Method

In accordance with the present invention, an aliphatic non-axial amino group is transformed into a corresponding hydroxylamino group. The formation of the hydroxylamino group is carried out by admixing an excess of a non-axial, aliphatic primary amine with a dialkyl dioxirane to form a reaction mixture. The dialkyl dioxirane utilized contains a total of two to about six carbon atoms in the two alkyl groups.

The reaction mixture so formed is maintained for a time period sufficient for the desired hydroxylamine product to form. The hydroxylamine product can thereafter be recovered or utilized in situ for another reaction such as formation of a hydroxamic acid by reaction with an acylating agent such as acetic anhydride.

An excess of the amine relative to the dialkyl dioxirane is used, with the molar ratio of non-axial, aliphatic primary amine to dialkyl dioxirane is about 5:1 to about 1.1:1, and more preferably about 2:1 to about 1.1:1.

Exemplary dialkyl dioxiranes include dimethyldioxirane, diethyldioxirane, methyl isopropyldioxirane, methyl propyldioxirane, ethyl sec-butyldioxirane and the like. 3,3-Dimethyldioxirane, also referred to herein as dimethyl dioxirane, contains a total of two carbon atoms in its alkyl groups and is utilized illustratively herein. Dimethyldioxirane is particularly preferred as the dialkyl dioxirane because its reaction product, acetone, is relatively readily removable from the reaction mixture.

The conversion of a primary aliphatic amine derivative to the corresponding hydroxylamine is carried out at a temperature of about $-50$ degrees C. with warming to about $+20$ degrees C. after the oxidation is complete and is typically carried out at a temperature of zero degrees C., or below. A non-reactive (inert) solvent such as acetone, methylene chloride-acetone or the like is utilized in the reaction mixture.

Preferably, the solvent boils at less than about 100 degrees C. so as to facilitate isolation and recovery of the hydroxylamine by merely removing the solvent, as with a stream of dry nitrogen or under reduced pressure and at a temperature below about 20 degrees C. Redissolution of solvent-free reaction mixture in a water-immiscible organic solvent such as methylene chloride, chloroform or benzene, followed by extraction with water having a pH value sufficient to protonate the unreacted amine but not protonate the hydroxylamine provides the purified hydroxylamine. Hydroxylamine has a $pK_a$ of about 6, whereas sugar amines such as glucosamine have a $pK_a$ value of about 7.75 and the contemplated amino acid derivatives have $pK_a$ values of about 7-8. Further purification of a hydroxylamine product can be effected by usual chromatographic techniques. The reaction product can also be chromatographically separated from unreacted amine without a prior extraction step.

The amine contemplated is aliphatic and is thus free from direct bonding to an aromatic group such as a phenyl or naphthyl group as would be the case for an aniline or naphthyl amine derivative. Indirect bonding to an aromatic ring as would be the case for a benzylamine derivative (one intervening bond) or a phenylalanine derivative (two intervening bonds) is contemplated for an aliphatic amine reactant.

The contemplated aliphatic amine is also a primary amine. Thus, the amino nitrogen atom is bonded to two hydrogen atoms and to an aliphatic organic group or moiety.

Whereas any aliphatic primary amine that can be dissolved in the reaction medium is contemplated, except for a reactant having an axial primary amine, equatorial amino sugar derivatives and derivatives of amino acids are particularly preferred. These particularly preferred amines are discussed in detail below.

Turning first to the sugar derivative, the amino group is present in other than an axial configuration; i.e., the amine is a non-axial primary amine. As is shown and discussed hereinafter, non-axial primary amines of sugar derivatives; i.e., those in an equatorial configuration for pyranose derivatives, and a non-axial/non-equatorial configuration for furanose derivatives, form the desired hydroxylamine derivative, whereas axial primary amines form oximes, as would otherwise be expected for the non-axial primary amines.

The sugar derivative can be a mono-, oligo- or polysaccharide. Hydroxylamine formation using exemplary mono- and oligosaccharide derivatives are illustrated herein.

A useful primary amine-containing sugar derivative sometimes referred to herein as an "amino sugar" or an "amino sugar derivative" can have a number of substituent groups, including one or more further sugar rings. Typically, each of the ring-bonded hydroxyl groups is reacted with a protecting group, as are any other substituent groups that are not desired to be oxidized such as additional nitrogen atoms or sulfur atoms.

Exemplary sugar ring substituent groups are discussed below. As will be seen, substantially any group that does not contain an atom that is oxidized under the reaction conditions or that inhibits dissolution of the sugar derivative in the reaction medium, such as an ionically charged group, can be present.

A starting equatorial primary amino sugar derivative utilized herein can be prepared by well known techniques. A useful amino sugar compound is referred to as being a derivative; i.e., the sugar molecule contains substituents in addition to the equatorial amino group. Cyclic sugar molecules are themselves hydroxyl-substituted tetrahydropyran or tetrahydrofuran derivatives. A useful amino sugar derivative can therefore be considered to be a dihydropyran or a 2,3-dihydrofuran derivative.

In view of the differing nomenclatures that can be utilized for sugar derivatives, and for clarity of expression, a hydroxyl group as would normally be present in a sugar molecule is referred to herein as a substituent. Similarly, hydrogen, which is normally present on a dihydropyran or 2,3-dihydrofuran, but is a substituent that can also replace a hydroxyl of a sugar, is also referred to herein as a substituent.

Each amino sugar derivative thus has a plurality of substituent groups. Exemplary, useful substituent groups include hydrogen, hydroxyl, $C_1$-$C_6$ alkyl, as well as protected hydroxyl, protected mercaptan and protected amine groups. Of the above substituents, hydrogen, hydroxyl, $C_1$-$C_6$ alkyl and protected hydroxyl (O-ether and O-acyl), protected mercaptan (S-acyl) and protected amine (acylated amine) groups are preferred.

Protected substituents are those that are reacted with another reagent to form a substituent that does not undergo reaction under the conditions of the oxidation. A group is also considered protected if it reacts, but can be readily regenerated as by reduction or ester formation. Most preferably, as where a glycoside such as an oligosaccharide is to be prepared that does not have protecting groups, a preferred protecting group is readily removable to provide the unprotected substituent with little or no alteration of the stereochemical configuration of the substituent or glycoside bonds.

Various types of ether-forming readily removable protecting groups are preferred for hydroxyl substituents, so that the substituents themselves are ethers. Particularly preferred readily removable ether linkages are benzyl or ring-substituted benzyl ethers having 7-10 carbon atoms, diaryl-$C_1$-$C_6$ alkylsilyl ethers such as diphenylmethylsilyl ether, aryldi-$C_1$–$C_6$ alkylsilyl ethers such as a phenyldimethylsilyl ether, and tri-$C_1$–$C_6$ alkylsilyl ethers such as trimethylsilyl and t-butyldimethylsilyl ethers. Acetals and ketals are also considered to contain ether linkages since each contains the C—O—C bond of an ether. Acetals and ketals formed from aldehydes or ketones containing 1 to about 12 carbon atoms such as formaldehyde, acetone, cyclohexanone, 1-decanal and 5-nonanone or an aromatic aldehyde such as benzaldehyde or naphthaldehyde or an aromatic ketone such as acetophenone. Acetone, formaldehyde and benzaldehyde are preferred for the preparation of ketals and acetals, respectively. Additional useful readily removable protecting groups are discussed in Kunz, *Angew. Chem. Int. Ed. Engl.*, 26: 294 (1988), whose disclosures are incorporated by reference.

The above-described readily removable substituents can be removed by a number of means well known in the art. For example, the benzyl ether-type protecting groups can be removed by hydrogenolysis over a palladium catalyst or by sodium or lithium in liquid ammonia. The various silyl ethers can be removed by reaction with tetrabutylammonium fluoride. The acetals and ketals can be removed with mild acids.

A useful equatorial primary amino sugar derivative can itself also be an oligosaccharide. Thus, an ether linkage can also be present between the amino sugar derivative and another substituted monosaccharide or oligosaccharide. This ether linkage is preferably between the anomeric carbon atom of the substituent sugar derivative and the amino sugar derivative, although such a glycosidic bond is not required. In this instance, the substituents on the amino sugar derivative are as described before along with one or more substituted saccharide units as further substituents; those substituted saccharide substituents also having substituents as described before.

Thus, an amino sugar derivative can be a substituted oligosaccharide. For example, a di- or tri-saccharide containing an equatorial primary amine can itself be a starting substituted amino sugar derivative useful herein.

It is neither always necessary nor desired that an ether substituent be readily removable. To that end, an O-ether can contain a $C_1$–$C_{18}$ alkyl, $C_6$–$C_{10}$ aryl or substituted aryl or non-benzyl $C_7$–$C_{10}$ aralkyl group bonded through an oxygen atom to the ring of a derivatized sugar molecule. Exemplary of such groups are methyl, ethyl, iso-propyl, cyclohexyl, lauryl and stearyl ethers, as well as phenyl, p-tolyl, 2-naphthyl, ethylphenyl, and 4-t-butylphenyl ethers. Oligosaccharides are another group of ether substituents that are not readily removed.

Other groups include $C_1$–$C_6$ alkyl and hydrogen. Exemplary $C_1$–$C_6$ alkyl groups include methyl, ethyl, iso-propyl, sec-butyl, cyclopentyl and n-hexyl groups.

When the amino sugar derivative is oxidized to form a corresponding hydroxylamine, it is important that the substituents not also be oxidized, or if oxidized, be readily reduced back to the original substituent. To that end, acyl protecting groups such as those formed by the reaction of a hydroxyl, mercaptan or amine group with a $C_1$–$C_{18}$ alkanoic acid such as acetic, stearic or cyclohexanoic acids or an aromatic acid such as benzoic, or 1-naphthaleneacetic acid (or formed from an anhydride, acid chloride or activated ester such as a N-hydroxysuccinimido ester of such an acid); i.e., a $C_1$–$C_{18}$ acyl group are also useful. A cyclic imide containing a total of 4–10 carbon atoms and 5–7 atoms in the imido ring such as succinimido, substituted succinimido like methylsuccinimido, phthalimido or a substituted phthalimide like 4-chlorophthalimido and a cyclic amide having 4–10 carbon atoms and 5–7 atoms in the amido ring such as pyrrolidinyl, valerolactamyl or caprolactamyl are also useful.

A useful starting substituted amino sugar compound is a sugar derivative that can be represented by the chemical formula wherein one of $R^1$, $R^2$, $R^3$, $R^9$ and $R^{10}$ is an equatorial primary amino group (—$NH_2$), and when other than a primary amino group;

$R^1$ is selected from the group consisting of hydroxyl (OH), hydrogen (H) $C_1$–$C_6$ lower alkyl, 2-furyl, $OR^4$, $NR^5R^6$ and $SR^{13}$;

$R^2$ is selected from the group consisting of H, $C_1$–$C_6$ alkyl, 2-furyl, $OR^4$, $NR^5R^6$ and $SR^{13}$;

$R^3$ is selected from the group consisting of H, $C_1$–$C_6$ alkyl, $(CH_2)_m OR^4$, 2-furyl, $OR^4$, $NR^5R^6$, $SR^{13}$, and or $R^3$ and $R^2$ form a cyclic acetal or ketal prepared from an aldehyde or ketone containing 1 to 12 carbon atoms;

m is zero, 1, 2, 3 or 4 (1–4) with the proviso that the number of carbon atoms in the glycal chain is not greater than 9, such that when m is zero, $R^3$ is $OR^4$, whereas when m is 1–4, m represents the number of methylene groups present;

n is zero or 1 such that when n is zero $R^2CH$ is absent, and when n is 1 $R^2CH$ is present;

$R^4$ is selected from the group consisting of hydrogen, $C_1$–$C_{18}$ alkyl, $C_6$–$C_{10}$ aryl, $C_1$–$C_{18}$ acyl, $C_7$–$C_{10}$ aralkyl, tri-$C_1$–$C_6$ alkylsilyl, diaryl-$C_1$–$C_6$ alkylsilyl, aryldi-$C_1$–$C_6$ alkylsilyl, and a substituted mono- or oligosaccharide;

$R^5$ is selected from the group consisting of $C_1$–$C_{18}$ alkyl, $C_6$–$C_{10}$-aryl, $C_7$–$C_{10}$ aralkyl, tri-$C_1$–$C_6$ alkylsilyl, aryl di-$C_1$–$C_6$ alkylsilyl, diaryl $C_1$–$C_6$ alkylsilyl, and $C_1$–$C_{18}$ acyl;

$R^6$ is selected from the group consisting of H, $C_1$–$C_{18}$ alkyl, $C_7$–$C_{10}$ aralkyl, and $C_1$–$C_{18}$ acyl with the proviso that (a) at least one of $R^5$ or $R^6$ of $NR^5R^6$ and $SR^6$ is

$C_1$–$C_{18}$ acyl, or (b) $NR^4R^5$ together form a cyclic amide or imide containing five to seven atoms in the ring and a total of 4–10 carbon atoms;

$R^7$ and $R^8$ are independently H or $C_1$–$C_9$ alkyl with the proviso that the number of carbon atoms in $R^7$ plus those of $R^8$ is nine or fewer;

$R^9$ is selected from the group consisting of hydrogen (H) or $C_1$–$C_6$ alkyl $OR^4$, $CO_2R^4$, CN, $CH_2OR^4$, 2-furyl, and $R^{10}$ is selected from the group consisting of hydrogen (H), $OR^4$, 2-furyl or $C_1$–$C_6$ alkyl; and $R^{13}$ is $C_1$–$C_{18}$ acyl.

A preferred $C_1$–$C_{18}$ alkyl group is a $C_1$–$C_6$ lower alkyl group. A preferred $C_1$–$C_{18}$ acyl group is a $C_1$–$C_6$ lower alkyl acyl group.

It is noted that hydrogen atoms are not shown bonded to the sugar ring carbon atoms linked to $R^1$, $R^3$, $R^9$ and $R^{10}$ in the above structural formula for purposes of clarity. Those hydrogen atoms are nevertheless present on the amino sugar derivative.

Examples of each of the above-described R groups, where the R can be more than a single group, are provided in the previous discussion. It is noted that for purposes of counting carbon atoms in a chain of a substituted glycal compound, $C_1$–$C_6$ alkyl and 2-furyl substituent groups are considered to be substituents and not part of the sugar backbone chain.

Of the various substituent groups that can be present on a non-axial primary amino sugar derivative, hydrogen, $C_1$–$C_6$ lower alkyl, $C_1$–$C_6$ lower alkyl O-ether, $C_1$–$C_6$ lower acyloxy, hydroxy, $C_1$–$C_{12}$ ketal and acetal and $C_4$–$C_{10}$ N-imido or cyclic amido having a ring containing five to seven atoms are preferred.

More specifically, an $R^1$, $R^2$, $R^3$, $R^9$ and $R^{10}$ group that is other than an equatorial primary amine group is preferably as follows:

(i) $R^9$ and $R^{10}$ are hydrogen;

(ii) $R^1$ and $R^2$ are independently selected from the group consisting of hydrogen, $C_1$–$C_6$ lower alkyl, O—$R^{14}$ where $R^{14}$ is selected from the group consisting of hydrogen, $C_1$–$C_6$ lower alkyl, $C_1$–$C_6$ acyl, before-described alkyl or alkylarylsilyl, substituted mono- or oligosaccharide, and $NR^{15}R^{16}$ where $NR^{15}R^{16}$ together form a cyclic amide or imide containing five to seven atoms in the ring and a total of 4–10 carbon atoms;

(iii) $R^3$ is selected from the group consisting of hydrogen, $C_1$–$C_6$ alkyl, $CH_2OR^{14}$, $OR^{14}$, where $R^{14}$ is as defined immediately above, and $R^7$ and $R^8$ are independently hydrogen or $C_1$–$C_9$ alkyl with the proviso that the number of carbon atoms in $R^7$ plus those in $R^8$ is nine or fewer;

(iv) $R^2$ and $R^3$ form a cyclic ketal or acetal prepared from a ketone or an aldehyde containing 1 to 12 carbon atoms; and (v) n is one (1).

A hydroxylamine reaction product corresponding to a non-axial amino sugar derivative of the above formula has a formula similar to that shown above except that the non-axial amino group is replaced by a non-axial hydroxylamino group (—NHOH).

For the amino acid derivatives, amine-containing carboxylic acid derivatives are contemplated. Both the D and L forms of the twenty naturally occurring amino acids are contemplated, as are the $C_1$–$C_{10}$ primary amino acids such as β-alanine (3-aminoproprionic acid), 6-aminocaproic acid, 8-aminocaprylic acid, 10-aminodecanoic acid, 3-aminobutyric acid, 2-aminocaprylic acid, 2-aminobutyric acid, 2-aminovaleric acid, 5-aminovaleric acid and α-aminopheylacetic acid. Of the amino acids, the naturally occurring twenty amino acids (both D and L forms) and several of those noted above contain the primary amino group at the 2- or α-position relative to the carboxyl group and those amino acid derivatives are particularly preferred, with derivatives of the twenty naturally occurring L amino acids and glycine being most preferred.

A contemplated amino acid is derivatized at its carboxylic acid portion to form a carboxylic ester or amide to assist in solubilizing the amino acid derivative in the reaction medium. Additional substituent groups can also be present, as already noted.

Preferred alcohol portions of the carboxylic ester are $C_1$–$C_6$ lower alkyl esters, although larger and aromatic ring-containing alcohols can be utilized. Exemplary $C_1$–$C_6$ lower alkyl alcohols include methanol, ethanol, n-butanol, iso-butanol and cyclohexanol, whereas aromatic ring-containing alcohols include phenol, benzyl alcohol and β-naphthol.

The carboxylic acid portion of the amino acid can also be an amide. The nitrogen atom of such an amide has the structure $NR^{11}R^{12}$.

$R^{11}$ and $R^{12}$ can be the same or different groups and are selected from the group consisting of: hydrogen, $C_1$–$C_6$ lower alkyl such as methyl, iso-propyl and hexyl, benzyl, phenyl, and $C_2$–$C_3$ hydroxy alkyl such as 2-hydroxyethyl and 3-hydroxypropyl; or $NR^{11}R^{12}$ can also together form a cyclic ring having a total of five or six atoms in the ring including the amido nitrogen such as where the ring is formed from piperidine, morpholine or pyrrolidene.

$NR^{11}R^{12}$ can also constitute the nitrogen atom, its bonded hydrogen atom and the residuum of another amino acid or polypeptide. Thus, a contemplated amino acid derivative can be, for example, the amino-terminal residue of a polypeptide containing two to about forty residues.

Where the amine to be transformed into a hydroxylamine is a portion of a polypeptide or where there is another substituent group present on the amino acid, the substituent group or groups present are free from ionic charge and are protected from oxidation as described previously for substituent groups present on a sugar derivatives.

Where $NR^{11}R^{12}$ is derived from an amino acid or polypeptide, the terminal carboxyl group is also present as an ester or amide as defined herein. Where the carboxyl group is an amide, the amido nitrogen atom has the formula NR$^{11}$R$^{12}$ except that neither of R$^{11}$ and R$^{12}$ is an amino acid or polypeptide residuum.

C. Results

1. Amino Sugars a. Mono- and Disaccharides

Figure 1:
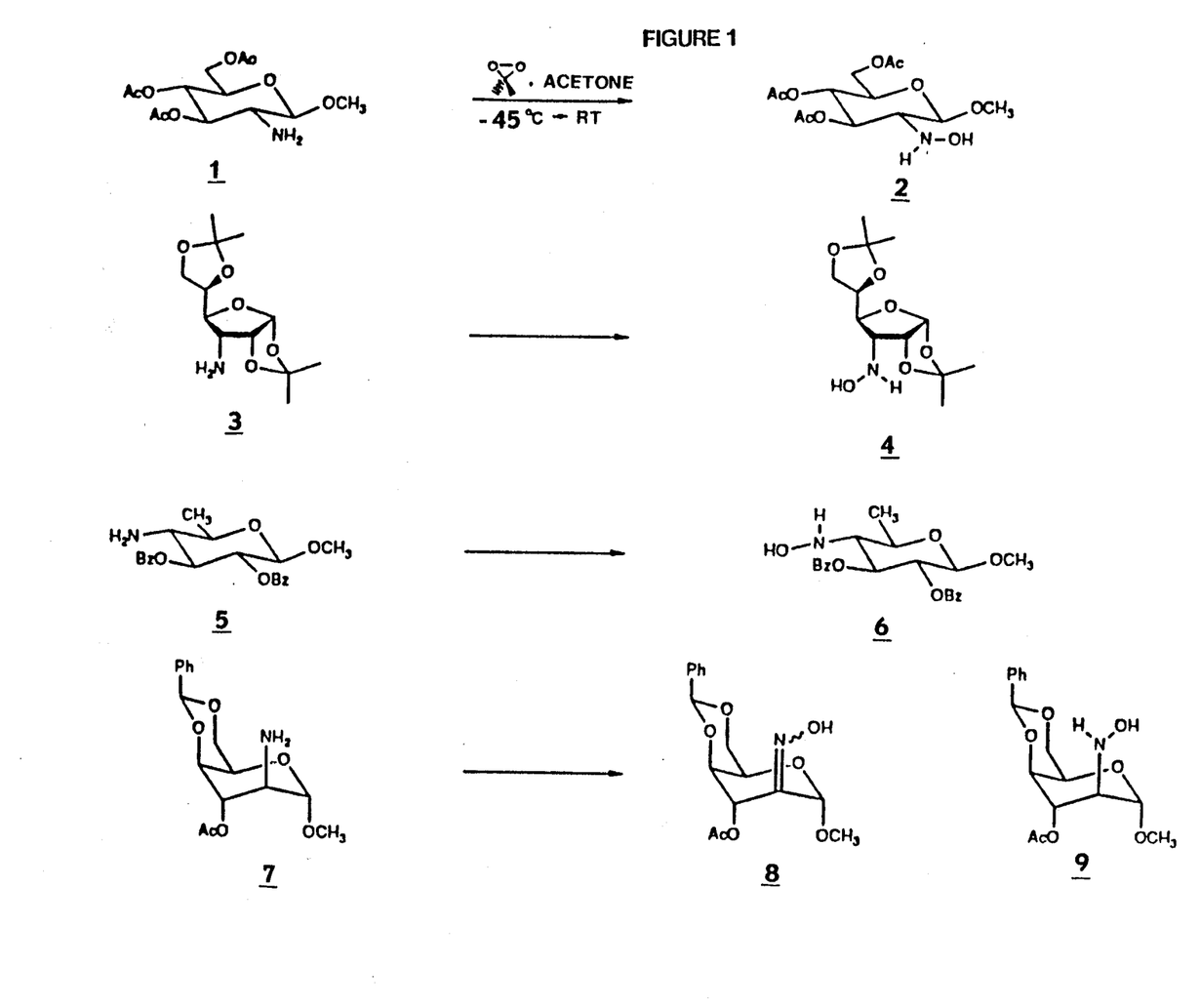
FIG. 1 illustrates the structures of some sugar-substituted primary amines and their corresponding hydroxylamine reaction products. Each reaction shown utilized dimethyl dioxirane as oxidant in an acetone solution at a temperature starting at −45 degrees C., which temperature was permitted to warm to ambient room temperature (RT) over a two-hour time period. In the structures, Ac is acetyl, Bz is benzoyl and Ph is phenyl. Wedge-shaped or heavily blackened bonds are utilized to indicate a bond projecting forward from the plane of the page, whereas dashed bonds indicate bonds projecting behind the plane of the page, following usual practice for such bonds.

Reaction of the β-methylglycoside of 3,4,6-triacetyl glucosamine Compound 1 [Yamasaki, et al., *Bull. Chem. Soc. Jpn.*, 49:3190 (1976)] with 2,2-dimethydioxirane as prepared by Murray et al., *J. Org. Chem.*, 50:2847 (1985) was carried out in acetone from −45°→ambient room temperature. There was isolated a 61 percent yield of the corresponding hydroxylamine Compound 2 (FIG. 1). The structure of Compound 2 follows from its NMR spectrum which indicates no change from Compound 1 in the number of multiplicity of carbon-bound protons (19), and its mass spectrum (m/e 335 which indicates a net gain of 16 mass units. In addition, there is observed a characteristic upfield shift (0.2 PPM) of the resonance of the proton on the carbon bearing the hydroxylamine relative to the corresponding amine.

Each hydroxylamine discussed has been characterized by $^1$H NMR, IR and high resolution mass spectrometry, which data are shown hereinafter.

Similarly, the 3-amino-allofuranose Compound 3 [Malik, et al., *J. Chem. Soc.; Chem. Commun.*, 22:1530 (1984)] afforded the corresponding hydroxylamine Compound 4 [Tronchet et al., *Helv. Chim Acta;* 69:1132 (1986)] (70 percent yield). The 4-amino-derivative Compound 5 [Stevens, et al., *J. Org. Chem.*, 39:298 (1974)] gave Compound 6 in 75 percent yield. (See, FIG. 1.)

Each of Compounds 1 and 5 contained its substituent primary amino group in an equatorial position. Substituents at the 3-position of the five-membered ring Compound 3 are neither axial nor equatorial, but assume a conformation therebetween.

The benzylidene 2-amino-idose derivative, Compound 7, [Guthrie, et al., *J. Chem. Soc.*, Perkin I, 650 (1974)], whose primary amino group is in an axial configuration, failed to react in the usual way. Instead of the expected Compound 9, there was obtained a mixture of starting material and oxime Compound 8 (FIG. 1). The structure of oxime Compound 8 was supported by the absence of one of the carbon bound protons and high resolution by mass spectroscopy.

Figure 2:
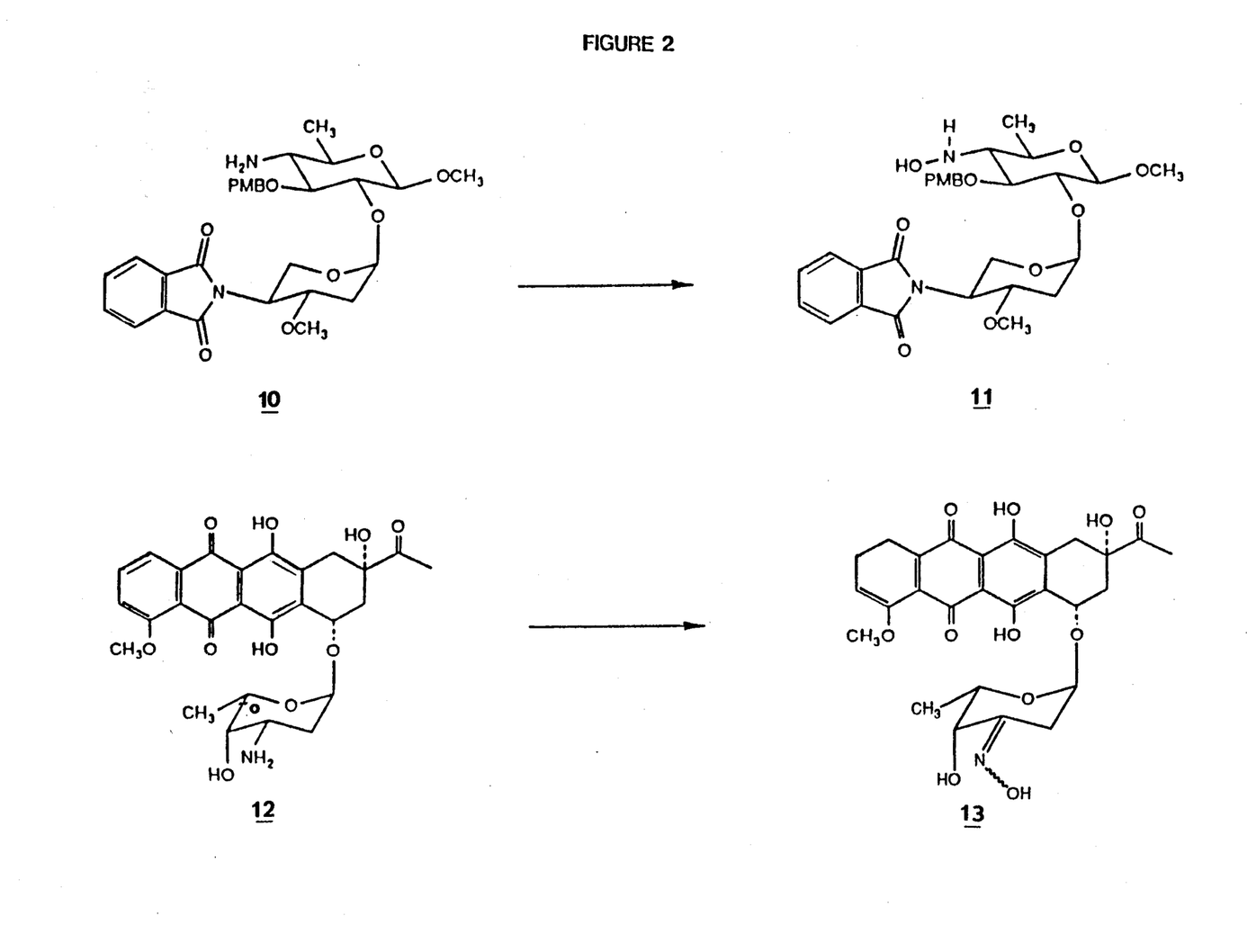
FIG. 2 illustrates further reactants, products for further exemplary oxidations. Here, PMBO represents p-methoxybenzyl. The same reaction conditions were used in the reaction of FIG. 2 as for FIG. 1. Bonds are as depicted in FIG. 1.

Although the applicability of the present method to the oxidation of axial amines remains to be demonstrated, two examples of oxidations of amines to provide complex hydroxylamines have been shown to be workable. Thus, disaccharide amine Compound 10 and daunomycin Compound 12 were oxidized to the corresponding hydroxylamine Compound 11 and the oxime Compound 13, presumably via the corresponding hydroxylamine (FIG. 2). It is believed that the quinoid groups participated in oxidation of the first-formed hydroxylamine into the observed oxime in daunomycin.

b. Trisaccharide and Chimeric Antibiotic

Figure 4:
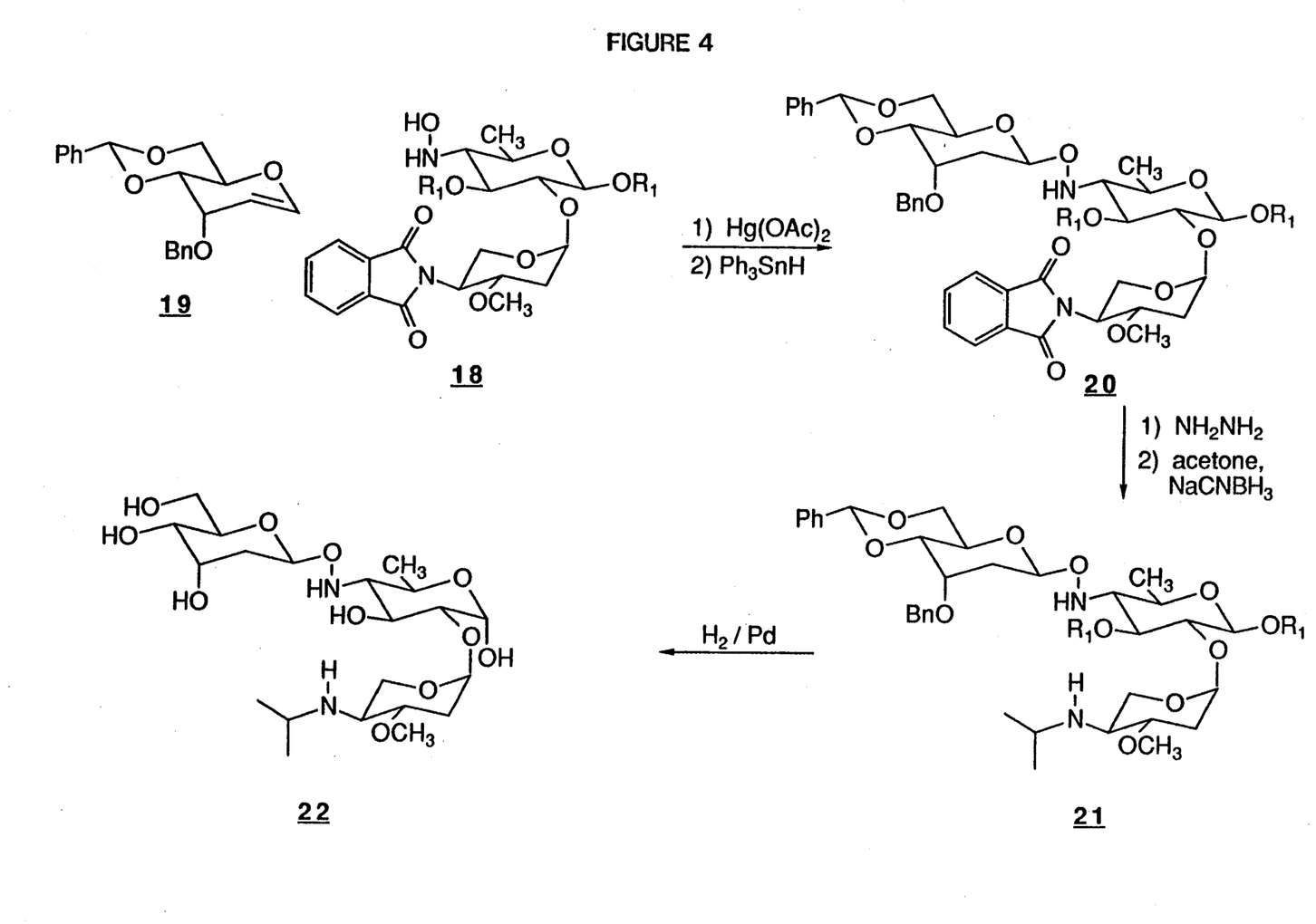
FIG. 4 illustrates a reaction scheme for the synthesis of a hydroxylamino trisaccharide similar in structure to the esperamicin trisaccharide, but lacking the thioether of that trisaccharide. In this figure, Ph is phenyl, Bn is benzyl, $R_1$ is p-methoxybenzyl, OAc is acetate and $H_2$/Pd is hydrogenation over a palladium catalyst.

FIG. 4 illustrates the synthesis of a trisaccharide similar to the esperamicin trisaccharide except for the sulfur-containing saccharide unit. Here, Compound 19 is reacted first with mercuric acetate [Hg(OAc)$_2$] and then with Compound 18 (prepared analogously to Compound 11). The resulting product is reacted with triphenylstannane (∅$_3$SnH) to form trisaccharide Compound 20. The allal derivative, Compound 19, can be prepared from the corresponding glucal derivative by the procedured discussed in Wittman et al., *J. Org. Chem.*, 55:1980 (March 1990).

Removal of the phthalimido group with hydrazine, followed by reductive alkylation with acetone and sodium cyanobarohydride provides the N-isopropylamino group (as is present in the esparamicin trisaccharide) of Compound 21. Thereafter, removal of the benyzlidene group and the p-methoxybenzyl group by hydrogenation over a palladium catalyst provides the unprotected trisaccharide, Compound 22. The unprotected trisaccharide, Compound 23, can then be reacted with an aglycone (ROH) such as that of daunorubicin or doxorubicin to form a chimeric antibiotic. This is discussed in greater detail hereafter in relation to FIG. 5.

Figure 5:
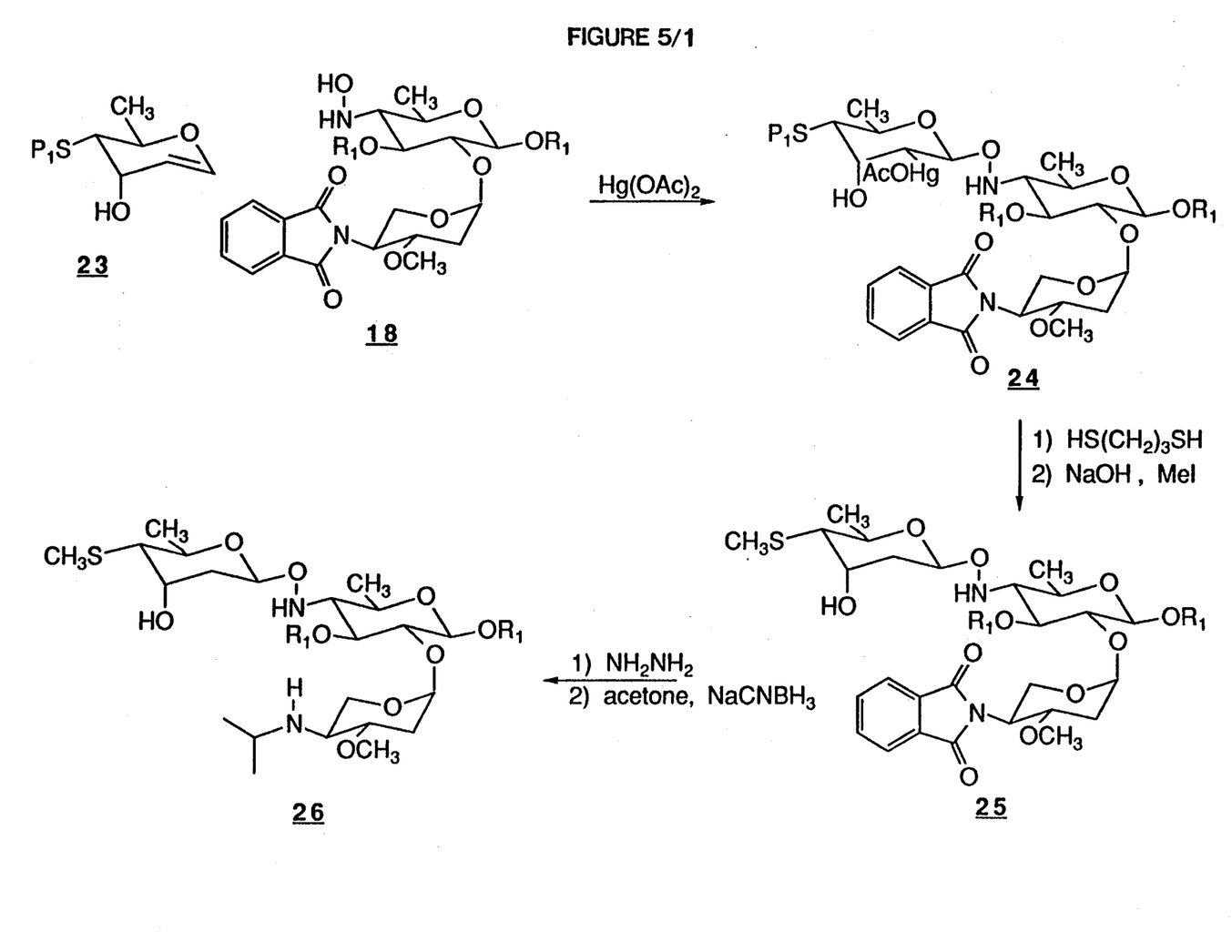
FIG. 5 in two sheets (FIG. 5/1 and FIG. 5/2) illustrates a reaction scheme for the preparation of an esperamicin trisaccharide, Compound 27, and a chimeric antibiotic, Compound 28, that utilizes that trisaccharide. In this scheme, $P_1$ is 2,4-dinitrophenyl, $R_1$ is p-methoxybenzyl, OAc is acetate, MeI is methyl iodide, DDQ is 2,3-dichloro-5,6-dicyano-1,4-benzoquinone and ROH is an exemplary aglycone such as daunorubicin or doxorubicin aglycone.

FIG. 5 illustrates the synthesis of an esperamicin trisaccharide and a chimetic antibiotic using the same. Compound 18 is used again, this time with Compound 23 that can be prepared as discussed in Wittman et al., *J. Org. Chem.*, 55:1980 (March 1990), wherein P$_1$ is 2,4-dinitrophenyl. Thus, Compounds 18 and 23 are reacted in the presence of mercuric acetate to form the trisaccharide Compound 24.

Removal of the protecting p-methoxybenzyl groups from Compound 26 with 2,3-dichloro-5,6-dicyano-1,4-benzoquinone (DDQ) provides the esperamicin trisaccharide, Compound 27. Reaction of Compound 27 with sodium hydride in trichloroacetonitrile followed by reaction of an aglycone (ROH) such as that from daunorubicin or esperamicin in boron trifluoride-etherate (BF$_3$—ET$_2$O) yields the chimetic antibiotic, Compound 28. Glycosylation of oligosaccharides using sodium hydride and trichloroacetonitrile followed by reaction of the resulting activated oligosaccharide with various alcohols in boron trifluoride-etherate is reviewed in Schmidt, *Angew. Chem. Int. Ed. (Engl.)*, 25:212 (1986).

2. Amino Acids

Figure 3:
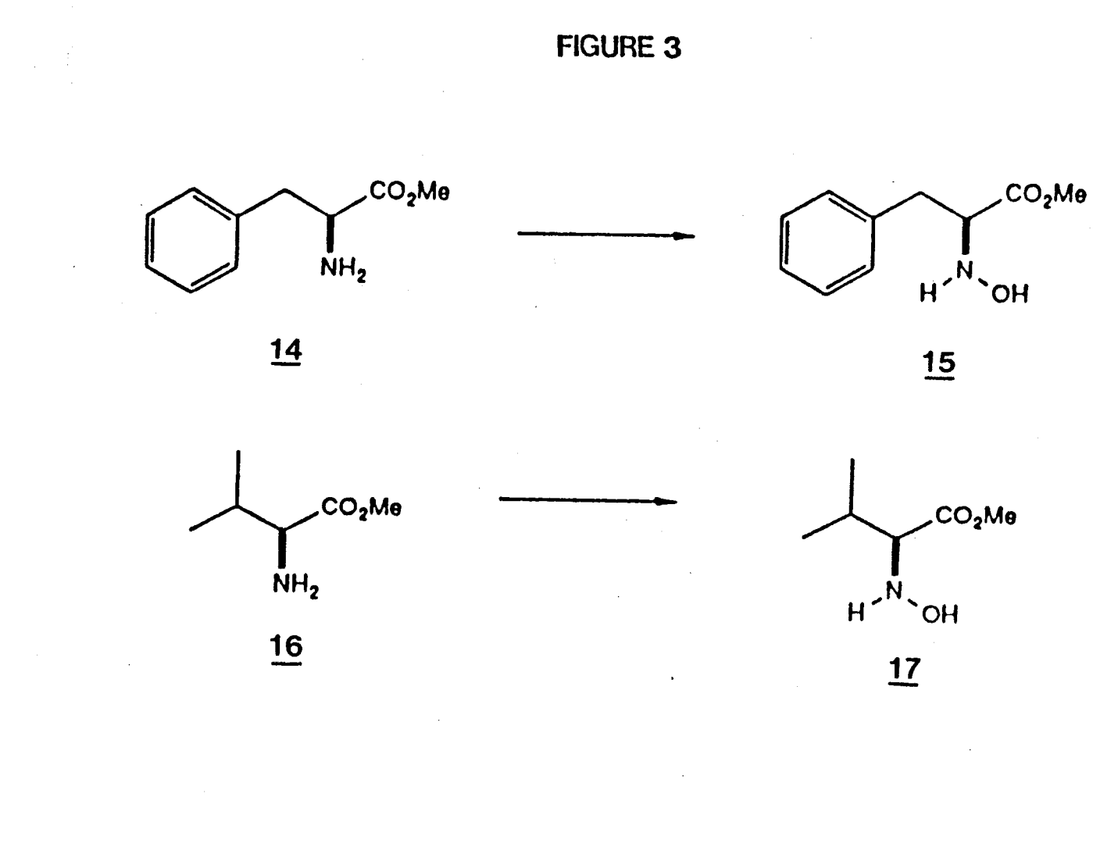
FIG. 3 illustrates the reactions of the methyl esters of phenylalanine, Compound 14, and valine, Compound 16, to their respective hydroxylamine derivatives, Compounds 15 and 17. The reaction conditions of FIG. 1 were utilized. Bonds are as depicted in FIG. 1.

It was of interest to explore the oxidation of other biologically interesting amines to hydroxylamines by the aforedescribed method. Oxidation of amino acid derivative Compounds 14 and 15 to Compounds 15 and 17 (FIG. 3) [Polonski et al., *Tetrahedron Lett.*, 28:2453 (1974)] respectively, illustrate an excellent future for this reaction.

BEST MODE FOR CARRYING OUT THE INVENTION

The method and products of this invention are illustrated in the examples that follow.

EXAMPLE 1

Methyl 3,4,6-tri-O-acetyl-2-deoxy-2-hydroxylamino-β-D-gluco pyranoside (Compound 2)

Compound 1 (41.0 mg) was dissolved in acetone (2.0 mL) and the resulting solution was cooled to −45° C. Dimethyldioxirane (1.2 mL, 0.10M) was added dropwise. The resulting reaction mixture was allowed to warm to ambient temperature over two hours. The reaction mixture was concentrated and chromatographed over silica gel (4:1 ethyl acetate (EtOAc)/hexanes) to provide 24.4 mg of hydroxylamine Compound 2.

mp 115°–116° C.; [α]D$^{25}$ +5.75° (CHCl$_3$, c, 1.105); IR (CHCl$_3$) 3500, 3020, 1745, 1370, 1240, 1040 cm$^{-1}$; $^1$H NMR (250 MHz, CDCl$_3$) δ 5.30 (t, 1H, J=9.58), 5.16 (t,

1H, J=9.67), 4.72 (d, 1H, J=8.02), 4.32 (dd, 1H, J=12.31, 4.72), 4.12 (dd, 1H, J=12.14, 2.42), 3.67–3.60 (m, 1H), 3.60 (s, 3H), 2.58 (dd, 1H, J=10.32, 8.06), 2.11 (s, 3H), 2.09 (s, 3H), 2.06 (s, 3H); $^{13}$C NMR (62.9 MHz, CDCl$_3$) δ 172.0, 170.8, 169.5, 99.9, 71.6, 70.3, 68.4, 65.3, 62.1, 57.5, 20.9, 20.8, 20.7; HRMS (CI): M+H calcd for C$_{13}$H$_{22}$NO$_9$: 336.1294. Found: 336.1281.

EXAMPLE 2

3-Deoxy-3-hydroxyamino-1,2:5,6-di-O-isopropylidine-α-D-allofuranose (Compound 4)

The 3-amino-3-deoxy-1,2:5,6-di-O-isopropylidine-α-D-allofuranose (Compound 3; 55 mg, 0.212 mmol) was dissolved in acetone (10 mL) and cooled to −45° C. The dimethyldioxirane (2.25 mL, 0.081M in acetone, 0.182 mmol) was added, and the resulting reaction mixture was left to warm to ambient temperature over two hours. The reaction mixture was concentrated and chromatographed over silica gel (1:1 hexane/ethyl acetate) to give 35 mg of the hydroxylamine Compound 4 (70 percent yield).

mp 135° C.; [α]D$^{25}$ 35.9 (CHCl$_3$, c, 2.7); IR (CHCl$_3$): 3200–3600 br, 1120 cm$^{-1}$; $^1$H NMR (250 MHz, CDCl$_3$) δ 5.82 (d, 1H, J=3.7 Hz), 4.81 (t, 1H, J=4.1, Hz) 4.19 (q, 1H, J=6.0 Hz), 4.06 (ABq, 1H, J=21.0, 8.4 Hz), 4.04 (ABq, 1H, J=12.0, 8.4 Hz), 3.76 (dd, 1H, J=9.4, 6.1 Hz), 3.49 (dd, 1H, J=9.4, 4.6 Hz), 3.20–2.20 (br s, 2H), 1.57 (s, 3H), 1.46 (s, 3H), 1.38 (s, 6H); HRMS (CI): M+H calcd for C$_{12}$H$_{21}$NO$_6$: 276.1448. Found: 276.1455.

EXAMPLE 3

Methyl 2,3-di-O-benzoyl-4,6-dideoxy-4-hydroxyamino-α-D-glucopyranoside (Compound 6)

Methyl 2,3-di-O-benzoyl-4,6-dideoxy-4-amino-α-D-glycopyranoside (Compound 5; 23 mg, 0.060 mmol) was dissolved in acetone (10 mL) and cooled to −45° C. To the amine was added the dimethyldioxirane (0.65 mL, 0.081M in acetone, 0.053 mmol). The resulting reaction mixture was slowly warmed to ambient temperature over two hours. The reaction mixture was concentrated and chromatographed over silica gel (3:2 benzene/ethyl ether) to give the hydroxylamine Compound 6 (18 mg, 85 percent).

[α]D$^{25}$ −47.8 (CHCl$_3$, c, 0.18); IR (CHCl$_3$): 3600–3300, 1735, 1290, 1125 cm$^{-1}$; $^1$H NMR (250 Mhz, CDCl$_3$) δ 7.99 (m, 2H), 7.52 (m, 1H), 7.39 (m, 2H), 5.64 (t, 1H, J=9.0 Hz), 5.51 (t, 1H, J=7.9 Hz), 5.35 (br s, 1H0, 5.27 (br s, 1H), 4.58 (d, 1H, J=7.9 Hz), 4.10 (m, 1H), 3.53 (s, 3H), 2.66 (t, 1H, J=9.4 Hz), 1.46 (d, 3H, J=6.2 Hz); HRMS (CI): M+H calcd for C$_{21}$H$_{23}$NO$_7$: 402.1553. Found: 402.1574.

EXAMPLE 4

Methyl-2-O-(4-N-Pthaloyl-2,4-dideoxy-3-O-methyl-α-L-threo-pentopyranosyl)-4,6-dideoxy-4-hydroxyamino-3-O-(4-methoxyphenyl)methyl-β-D-glucopyranoside (Compound 11)

To a solution of the amino disaccharide (Compound 10; 25 mg, 0.045 mmol) in acetone (10 mL) at −45° C. was added the dimethyldioxirane (0.45 mL, 0.090M in acetone, 0.041 mmol). The reaction mixture was slowly warmed to ambient temperature over two hours. The reaction mixture was concentrated and chromatographed over silica gel (1:1 hexanes/ethyl acetate) to give the hydroxylamine Compound 11 (22.5 mg, 85 percent).

[α]D$^{25}$ −56.8 (CHCl$_3$, c, 1.45); IR (CHCl$_3$): 1720, 1520, 1395, cm$^{-1}$; $^1$H NMR (250 MHz, CDCl$_3$) δ 7.85 (m, 2H), 7.74 (m, 2H), 7.32 (d, 2H, J=8.6 Hz), 6.92 (d, 2H, J=8.6 Hz), 5.42 (d, 1H, J=2.9 Hz), 4.78 (ABq, 2H, J=21.5, 10.9 Hz), 4.74 (t, 1H, J=11.3 Hz), 4.56 (dt, 1H, J=10.4, 4.2 Hz), 4.32 (d, 1H, J=7.9 Hz), 4.30 (m, 1H), 3.99 (t, 1H, J=9.7 Hz), 3.82, (s, 3H), 3.71 (m, 1H), 3.59 (s, 3H), 3.51 (m, 2H), 3.24 (s, 3H) 2.80–2.00 (br s, 2H), 2.36 (t, 1H, J=9.7 Hz), 2.36 (m, 1H), 1.61 (m, 1H), 1.37 (t, 3H, J=6.1 Hz); HRMS (CI): M+H calcd for C$_{29}$H$_{36}$N$_2$O$_{10}$: 573.2449. Found: 573.2459.

EXAMPLE 5

N-hydroxylamino Methyl-D-Phenylalanine (Compound 15)

To a solution of L-phenylalanine methyl ester (Compound 14; 33 mg. 0.184 mmol) in acetone (8 mL) at −45° C., was added the dimethyldioxirane (1.9 mL, 0.089M in acetone, 0.169 mmol). The resulting reaction mixture was slowly warmed to ambient temperature over two hours. The solution was concentrated and chromatographed over silica gel (3:1 hexanes/ethyl acetate) to give the hydroxamic acid methyl ester Compound 17 (18 mg. 54 percent) as a white solid.

mp 64°–65° C.; [α]D$^{25}$ 16.6° (C$_6$H$_6$, c, 1.51); IR (CHCl$_3$): 3500–3000 br, 1730, 1430, 1215 cm$^{-1}$ $^1$H NMR (250 MHz, CDCl$_3$) δ 7.35–7.18 (m, 5H), 5.35 (br s, 2H), 3.90 (dd, 1H, J=8.4, 5.8 Hz), 3.75 (s, 3H), 3.03 (dd, 1H, J=13.9, 5.8 Hz), 2.91 (dd, 1H, J=13.9, 8.5 Hz).

EXAMPLE 6

N-Hydroxylamino Methyl-D-Valine (Compound 17)

To a solution of L-valine methyl ester (Compound 16; 30 mg, 0.229 mmol) in acetone (10 mL) at −45° C. was added the dimethyldioxirane (2.30 mL, 0.089 in acetone, 0.205 mmol). The resulting reaction mixture was slowly warmed to ambient temperature over two hours. The solution was concentrated, dissolved in THF (5 mL) and treated with concentrated HCl. The solution was concentrated to give a white solid Compound 17 decomposing at 2158°–159° C. (31 mg, 82 percent). The solid was recrystallized from MeOH/H$_2$O.

mp 158°–159° C. (dec); [α]D$^{25}$ 30.7° (MeOH, c, 0.69); IR (CHCl$_3$): 3500–3000 br. 1725, 1430, 1210, 1010 cm$^{-1}$; $^1$HNMR (250 MHz, CDCl$_3$) δ 5.80–4.50 (br s, 2H), 3.78 (s 3H), 3.46 (d, 1H, J=6.7 Hz), 1.90 (m, 1H), 0.96 (dd, 6H, J=6.8, 5.3 Hz).

ANALYTICAL DATA RELATING TO OTHER COMPOUNDS

Methyl 3-O-acetyl-4-6-O-benzylidene-2-hydroxyimino-α-D-xylo-hexopyranoside (Compound 8)

1:1 mixture of E and Z isomers. IR (CHCl$_3$): 3520, 3010, 2930, 1740, 1370, 1240, 1140, 1080, 1020, cm$^{-1}$; $^1$H NMR (250 MHz, CDCl$_3$) δ 7.57–7.52 (m, 4H), 7.36–7.30 (m, 6H), 6.20 (m, 1H), 5.64 (s, 1H), 5.5s (s, 1H), 5.51 (d, 1H, J=0.85), 5.41 (d, 1H, J=1.36), 4.53 (d, 1H, J=1.49), 4.51 (m, 2H), 4.45 (d, 1H, J=1.26), 4.42 (d, 1H, J=1.45), 4.23 (dd, 1H, J=5.75, 2.11), 4.18, (dd, 1H, J=4.73, 1.98), 3.61 (s, 1H), 3.51 (m, 1H), 3.43 (m, 1H), 2.08 (s, 3H), 2.02 (s, 3H); HRMS (CI): M+H calcd for C$_{16}$H$_{22}$NO$_7$: 338.1240. Found: 338.1252.

Daunomycin Oxime (Compound 13)

mp 167°–169° C.; $^1$H NMR (250 MHz, CDCl$_3$) δ 14.00 (s, 1H), 13.32 (s, 1H), 8.05 (d, 1H, J=7.2 Hz), 7.80 (t, 1H J=8.0 Hz), 7.41 (d, 1H, J=8.0 (Hz), 7.00 (s, 1H), 5.67 (d, 1H, J=3.2 Hz), 5.37 (br s, 1H), 4.60 (s, 1H), 4.40 (br d, 1H), 4.10 (s, 3H), 4.05 (m, 1H), 3.96 (s, 1H), 3.16 (ABq, 1H, J=61.8, 19.0 Hz), 2.91 (dt, 1H, J=13.2, 3.6 Hz), 2.42 (s, 3H), 2.40 (m, 1H) 2.15 (m, 1H), 2.07 (m, 1H), 1.71 (m, 1H), 1.38 (d, 3H, J=6.4 Hz); $^{13}$C NMR (62.9 MHz, CDCl$_3$) δ 211.3, 186.8, 186.6, 161.0, 156.3, 155.6, 135.7, 135.4, 134.4, 134.0, 120.8, 119.7, 118.5, 111.4, 111.3, 100.2, 76.8, 69.4, 68.9, 68.3, 59.2, 56.6, 34.8, 33.3, 24.6, 20.0, 16.5.

The foregoing is intended as illustrative of the present invention but not limiting. Numerous variations and modifications may be effected without departing from the true spirit and scope of the invention.

We claim:

1. A process for forming an aliphatic non-axial hydroxylamine from a corresponding aliphatic non-axial primary amine that comprises admixing an excess of an aliphatic non-axial primary amine with a dialkyl dioxirane having a total of two to about six carbon atoms in the dialkyl groups in a non-reactive solvent at a temperature in the range of about zero to −50 degrees C. to form a reaction mixture, and maintaining said reaction mixture at said temperature for a time period sufficient for a corresponding hydroxylamine to be formed; and     recovering the formed corresponding aliphatic non-axial hydroxylamine.

2. The process according to claim 1 wherein said aliphatic non-axial primary amine is present in an amino acid.

3. The process according to claim 2 wherein the amino acid aliphatic non-axial primary amine is the α-amino group.

4. The process according to claim 1 wherein said aliphatic non-axial primary amine is present as a substituent of a sugar.

5. The process according to claim 1 wherein said dialkyl dioxirane is dimethyl dioxirane.

6. A process for converting a non-axial primary amino group of a sugar into a non-axial hydroxylamino group of a sugar that comprises admixing an excess of an aliphatic non-axial primary amino substituted sugar with a dialkyl dioxirane having a total of two to about six carbon atoms in the dialkyl groups in a non-reactive solvent at a temperature in the range of about zero to −50 degrees C. to form a reaction mixture, and maintaining said reaction mixture at said temperature for at time period sufficient for a hydroxylamine to be formed; and     recovering the formed aliphatic non-axial hydroxylamine sugar.

7. The process according to claim 6 wherein said dialkyl dioxirane is dimethyl dioxirane.

8. The process according to claim 6 wherein said sugar is selected from the group consisting of a glucose, allofuranose, rhamnose, and daunosamine.

9. A process of converting the α-amine of an α-amino acid into to an α-hydroxylamine that comprises admixing an α-amino acid with a dialkyl dioxirane having a total of two to about six carbon atoms in the dialkyl groups in a non-reactive solvent at a temperature in the range of about zero to −50 degrees C. to form a reaction mixture, and maintaining said reaction mixture at said temperature for a time period sufficient for a hydroxylamine to be formed; and     recovering the formed α-hydroxylamine amino acid derivative.

10. The process according to claim 9 wherein said dialkyl dioxirane is dimethyl dioxirane.

11. The process according to claim 9 it wherein said amino acid is derivatized at its carboxylic acid position to fore a $C_1$–$C_6$ lower alkyl carboxylic ester or an amide whose nitrogen atom has the structure $NR^{11}R^{12}$, where $R^{11}$ and $R^{12}$ are independently selected from the group consisting of hydrogen, $C_1$–$C_6$ lower alkyl, benzyl, phenyl and $C_2$–$C_3$ hydroxyalkyl or $NR^{11}R^{12}$ together form a cyclic ring having a total of five or six atoms in the ring including the amido nitrogen, or $NR^{11}R^{12}$ is pan of the residuum of an amino acid or polypeptide whose terminal carboxylic acid portion is derivatized to fore an ester or an amide whose nitrogen atom has the structure $NR^{11}R^{12}$.

12. The process according to claim 11 wherein said amino acid is present as a methyl ester.

13. The process according to claim 12 wherein said amino acid is a methyl ester of phenylalanine or valine.

* * * * *